(12) United States Patent
Berthonnaud et al.

(10) Patent No.: US 7,361,150 B2
(45) Date of Patent: Apr. 22, 2008

(54) METHOD AND DEVICE FOR EVALUATING THE BALANCE FORCES OF THE SKELETON

(75) Inventors: Eric Berthonnaud, Charbonnieres les Bains (FR); Joannes Dimnet, Caluire Et Cuire (FR); Pierre Roussouly, Saint Cyr au Mont d'Or (FR)

(73) Assignee: Warsaw Orthopedic, Inc., Warsaw, IN (US)

( * ) Notice: Subject to any disclaimer, the term of this patent is extended or adjusted under 35 U.S.C. 154(b) by 42 days.

(21) Appl. No.: 10/877,114

(22) Filed: Jun. 25, 2004

(65) Prior Publication Data

US 2004/0228510 A1 Nov. 18, 2004

Related U.S. Application Data

(63) Continuation of application No. PCT/FR02/04541, filed on Dec. 24, 2002.

(30) Foreign Application Priority Data

Dec. 28, 2001 (FR) .................................. 01 17126

(51) Int. Cl.
A61B 5/103 (2006.01)
A61B 5/117 (2006.01)
(52) U.S. Cl. ...................... 600/595; 33/515; 73/379.01
(58) Field of Classification Search ................ 600/587, 600/594, 595, 368, 424, 425, 436; 33/515; 73/379.01, 383
See application file for complete search history.

(56) References Cited

U.S. PATENT DOCUMENTS

| | | | | |
|---|---|---|---|---|
| 4,277,828 A * | 7/1981 | Tateishi | ...................... | 600/587 |
| 4,655,227 A * | 4/1987 | Gracovetsky | ................ | 600/594 |
| 4,791,934 A * | 12/1988 | Brunnett | ...................... | 600/429 |
| 4,832,049 A * | 5/1989 | Matsushita et al. | .......... | 600/594 |
| 4,971,069 A * | 11/1990 | Gracovetsky | ................ | 600/594 |
| 5,080,109 A * | 1/1992 | Arme, Jr. | ..................... | 600/595 |
| 5,198,669 A * | 3/1993 | Namiki et al. | ............... | 250/587 |
| 5,388,591 A * | 2/1995 | De Luca et al. | ............. | 600/592 |
| 5,841,830 A * | 11/1998 | Barni et al. | ................... | 378/15 |
| 6,049,584 A * | 4/2000 | Pfeiffer | ......................... | 378/39 |
| 6,282,306 B1* | 8/2001 | Inoue et al. | ................. | 382/132 |
| 6,423,015 B1* | 7/2002 | Winkenbach et al. | ........ | 600/587 |
| 6,514,219 B1* | 2/2003 | Guimond et al. | ............ | 600/595 |
| 2003/0004438 A1 | 1/2003 | Berthonnaud et al. | | |

FOREIGN PATENT DOCUMENTS

| | | |
|---|---|---|
| EP | 0 119 660 | 9/1984 |
| FR | 2 803 507 | 7/2001 |
| NL | 7 415 910 | 6/1976 |

* cited by examiner

Primary Examiner—Max Hindenburg
Assistant Examiner—Rene Towa
(74) Attorney, Agent, or Firm—Haynes and Boone, LLP

(57) ABSTRACT

The invention concerns a method which consists in producing a radiographic image of the skeleton to be studied, determining the position of the body's global axis of gravity (5), selecting on the image segments of the skeleton (S1-S7) to be considered and their articulations (A5), locating the main tensor muscles (M1-M6, M62), and determining by calculation the intensity of the return forces exerted by said tensor muscles to compensate the gravitational force.

12 Claims, 5 Drawing Sheets

METHOD AND DEVICE FOR EVALUATING THE BALANCE FORCES OF THE SKELETON

CROSS-REFERENCE TO RELATED APPLICATIONS

This application is a continuation of co-pending International Application No. PCT/FR02/04541 filed Dec. 24, 2002, the disclosure of which is incorporated herein by reference.

TECHNICAL FIELD OF THE INVENTION

The present invention concerns evaluation of the muscular and articular forces in a subject occupying a stable posture.

The anatomy of living beings has been analyzed for a long time, particularly in order to determine therefrom the skeleton with its articulations and the muscles which control its movements.

In particular, the shape of the skeleton, the possible ranges of movement, the attachment points of the muscles and the range of their movements are known.

Yet virtually nothing is known about the values of the muscular forces giving rise to the movements.

Neither is anything known about the values of the muscular forces necessary for acquiring and maintaining a stable posture in a living being, or about the articular forces which are induced. Excessive muscular and/or articular forces, however, certainly give rise to fatigue, functional disorders and degradation of the articulations, so that it is of interest to evaluate these forces.

DESCRIPTION OF THE INVENTION

The problem addressed by the present invention is to provide a novel method, and a novel device, for evaluating the balance forces of the skeleton, or muscular forces involved in acquiring and maintaining a stable posture, and for evaluating the articular forces which result from this.

The invention derives from the viewpoint according to which, for a human being occupying a stable posture, each of the constituent body segments is assumed to be balanced on the segment below by means of the muscular forces which counterbalance the effect of gravity. As for analysis of the relative movements between the segments, the following segments are assumed to be indeformable: head, forearms, arms, feet, legs, thighs. Contrary to the analysis of movements, in which the torso is considered as a virtually rigid single unit, the invention recognizes that the torso consists of a cervical segment, corresponding to the cervical column, a dorsal segment corresponding to the dorsal column, a lumbar segment corresponding to the lumbar column, and the pelvis. The invention adopts the viewpoint according to which a stable posture is never rigid; there can be instantaneous posture corrections which do not modify the cervical, dorsal or lumbar curvatures, but which affect their relative angular positions.

For evaluation of the muscular and articular forces, the invention uses two items of prior information.

The first item of information concerns the shape and the relative position of the body segments when they are balanced. The morphology of the constituent body segments and their relative positions are obtained by means of a radiographic exposure. The articulated extremities of each skeleton segment, and their relative positions, are thus determined.

The second item of prior information concerns the gravitational forces applied to the body structure, which tend to imbalance it. This information is sought in the form of the overall axis of gravity, which passes through the subject's overall center of gravity when he or she is in a balanced posture, and the position of which is generally offset with respect to the skeleton.

In an overall posture, therefore, the head is assumed to constitute the end segment, which is firstly balanced with respect to the segment underneath, consisting of the cervical segment. Together, the head and the cervical segment are balanced on the next segment, consisting of the dorsal segment. In their turn, all the articulations between groups of upper and lower segments are balanced by descending balance. Finally, the entire body as a whole is balanced around the ankle.

Accordingly, in order to evaluate the muscular and articular balance forces of a subject's skeleton, the invention provides a method comprising the following steps:

a) producing a radiographic image of the skeleton to be studied, taken in a plane generally perpendicular to the rotation axes of the articulations of the skeleton to be studied, b) simultaneously determining the position of the overall axis of gravity of the body on the radiographic image, c) selecting the skeleton segments articulated to one another on the radiographic image, identifying their positions and those of the articulations, and assigning the weight of the corresponding body segment to each segment, d) identifying the directions and anchoring points on the radiographic image of the main tensor muscles balancing the skeleton to be studied, and e) determining the intensity of the restoring force exerted by the main tensor muscles by calculation, assuming that it compensates for the rotational moment of the force of gravity applied to each segment about the lower articulation of said segment.

Preferably, the method furthermore determines the bearing force of each segment on its lower articulation by calculation, assuming that it is equal to the resultant of the force of gravity and of the restoring force applied to the segment.

In practice, the following procedure is adopted for carrying out such an evaluation method:

some or all of the following segments are selected as articulated segments: the head, the cervical segment, the dorsal segment, the lumbar segment, the pelvic segment, and the femurs; and for the balancing, the following are considered as main balancing tensor muscles: the main lateral and median agonist, antagonist muscles. These muscles recruited to participate in balance are selected by the clinical user as a function of the spine-pelvis complex posture.

Slight movements by the subject may advantageously be taken into account when he or she is placed in a stable balance position. To that end, the successive positions of the overall axis of gravity for a few seconds are stored with a frequency of several acquisitions per second, the set of stored positions constituting an elliptical cloud of positions. The dispersion ellipse which envelopes said cloud of positions is determined, and the radiographic images corresponding to an overall axis of gravity whose position lies in the dispersion ellipse are selected.

The error in the evaluation of the restoring or bearing forces may also be determined by calculation as a function of the dispersion ellipse.

An embodiment of the invention is a device for evaluating the balance forces of the skeleton, that comprises:

an X-ray source and support means for a target plate sensitive to X-rays, a subject support plate, designed to support the subject in a fixed position between the X-ray source and the target-plate support means and to generate image position signals of the horizontal position of the overall axis of gravity of the subject, means for digitizing the radiographic image of the subject on the target plate, so as to generate a digitized radiographic image which is stored in a suitable memory, means for superimposing the digitized image of the shadow, cast by the overall axis of gravity on the target plate, onto the digitized radiographic image of the subject, means for selecting, on the digitized radiographic image, the articulated skeleton segments and their articulations, as well as the anchoring points of the balancing tensor muscles, and computation means and a program for calculating the intensity of the restoring force exerted by the balancing tensor muscles, assuming that it compensates for the rotational moment of the force of gravity applied to each segment about the lower articulation of said segment.

In another embodiment, the device for evaluating the balance forces of the skeleton further comprises means for evaluating the variations in the subject's vertical posture, by the dimensions of the horizontal-position dispersion ellipse of his or her overall axis of gravity, when he or she occupies a stable position.

According to an advantageous embodiment, the program comprises one or more acquisition sequences according to which:

the operator picks the positions on the radiographic image of the articulations, the segments and the anchoring points of the balancing tensor muscles, and the means for digitizing the radiographic image of the subject store the positions picked by the operator in the memory.

BRIEF DESCRIPTION OF THE DRAWINGS

Other objects, characteristics and advantages of the present invention will become apparent from the following description of particular embodiments, which is provided with reference to the appended figures in which.

DESCRIPTION OF THE PREFERRED EMBODIMENTS

Figure 7:
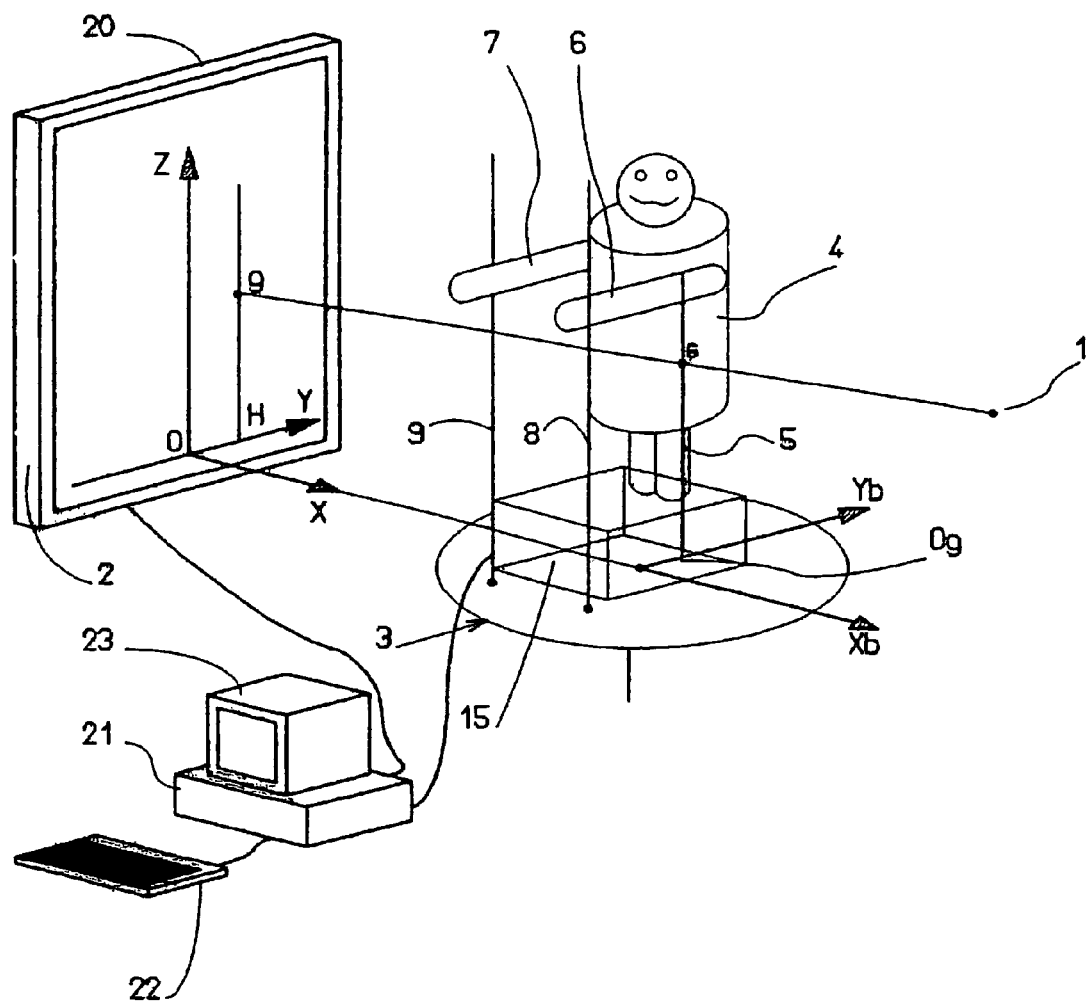
FIG. 7 is a schematic perspective view of a device according to the invention for taking radiographic exposures, with determination of the overall axis of gravity.
Figure 8:
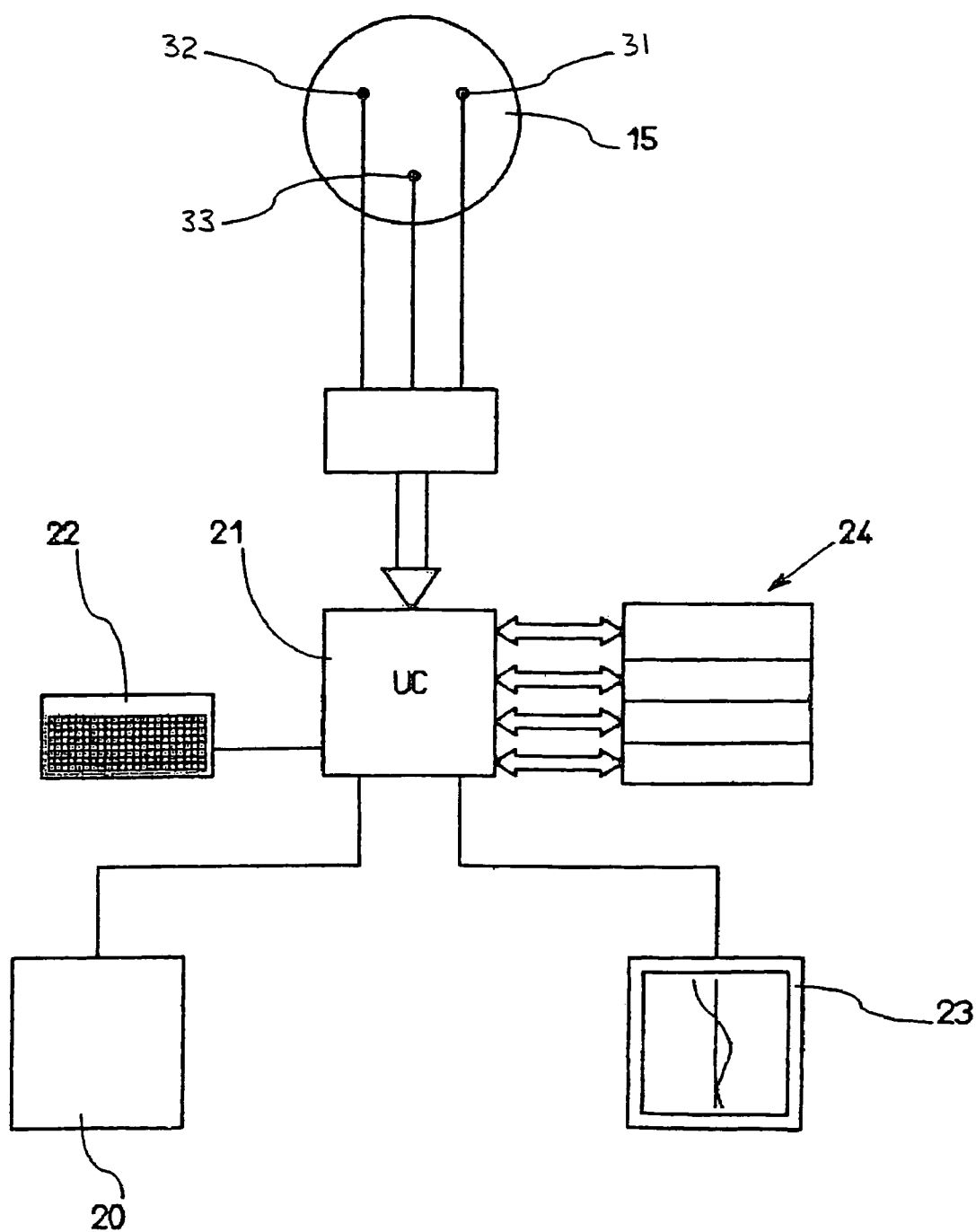
FIG. 8 is a theoretical scheme illustrating the essential computation means for evaluating the balance forces according to the invention.

The device illustrated in FIG. 7 will be considered first, for example making it possible to acquire the data for analyzing the standing posture of a subject 4.

The device comprises an X-ray source 1, support means for a target plate 2 for supporting a target plate which is sensitive to X-rays and is oriented vertically at a certain horizontal distance from the X-ray source 1, and subject support means 3 designed to support a subject 4 in a fixed position between the X-ray source 1 and the support means for the target plate 2. The device is thus a system for taking radiographs. The X-ray source 1 and the support means for the target plate 2 may have a structure such as those conventionally used in medical radiography systems.

In the device of FIG. 7, the subject support means 3 comprise means for detecting the horizontal position of the support plane and for identifying the instantaneous position of the overall axis of gravity 5 of the subject 4, or vertical axis passing through the center of gravity G of the subject 4, in this plane while the X-ray source 1 is operating. The instantaneous overall axis of gravity 5 is acquired when the radiographic exposure is being taken, and its position is projected into the plane of the radiographic image from the X-ray source 1 along a conical projection. A principle for position sensing of the overall axis of gravity and projection onto the radiographic image is described in Document WO 01/50956 or its equivalent FR 2 803 507 A.

For example, the subject support means 3 comprise a modified balance-force plate 15 provided with a plurality of force sensors 31,32,33, which are distributed horizontally at positions identified with res-pect to a frame Xb Yb and are associated with computation means 21 for calculating the position Og, in the horizontal plane, of the resultant of the forces applied by the subject 4 onto the force plate 15 in the frame Xb Yb. The computation means 21 may, for example, be the computation unit of a microcomputer that also has a display screen 23 and a keyboard 22.

In the standing position, the arms 6 and 7 of the subject 4 may be left free. As an alternative, it may be beneficial to provide supports 8 and 9 on which the subject can place his or her hands or arms, so as to determine a stable and reproducible position of the subject 4.

In the device of FIG. 7, means 20 are furthermore provided in order to digitize the radiographic image of the subject on the support means for the target plate 2 by scanning. A scanner may be used for this which is suitable for analyzing the radiographic image produced on the X-ray sensitive target plate 2 by scanning, and for producing a sequence of digital signals constituting the digitized radiographic image. This image is sent to the computation means 21, which store and process it.

The processing comprises, in particular, an operation that consists in superimposing the image of the shadow Hg, cast by the overall axis of gravity 5 of the subject on the target plate 2 containing the radiographic image, onto the radiographic image of the subject. This superposition may be carried out by the computation means 21, which receive the information about the coordinates of the horizontal projection Og of the center of gravity G from the force plate 15, which deduce the position of the cast shadow Hg therefrom and which introduce this into the digitized image contained in the memory 24.

Such a device may be like the one described in Document WO 01/50956, to which reference may be made for further details.

FIGS. 1 to 4 will now be considered in order to better understand the force evaluation method according to the invention, and the operation of the device of FIG. 7.

Figure 1:
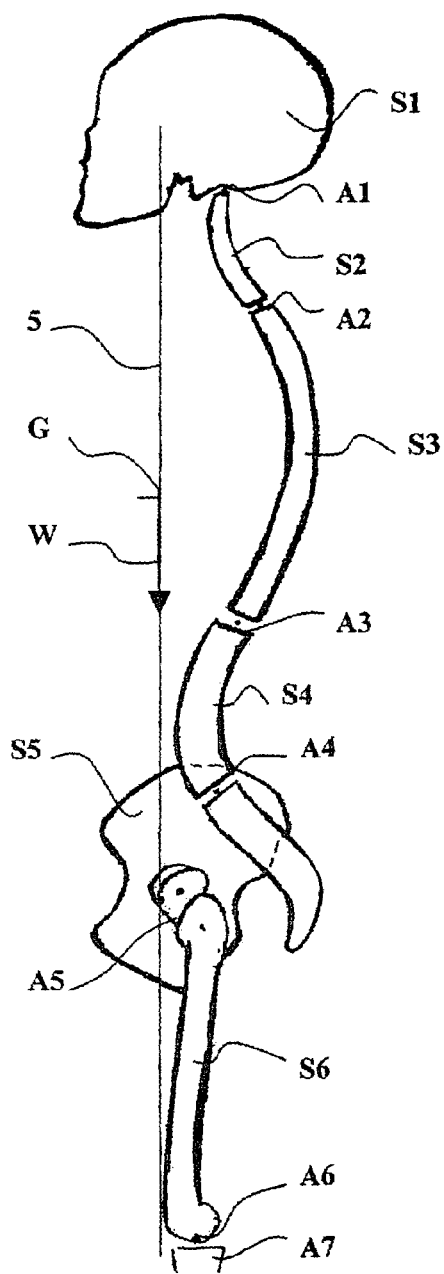
FIG. 1 is a side view illustrating the main body segments of the human body, with their articulations and the position of the overall axis of gravity of the body.

FIG. 1 schematically represents the shape of the main segments of the human skeleton, their relative positions and the articulation points. For instance, the upper segment S1 formed by the head, the second segment S2 formed by the cervical column, the third segment S3 formed by the dorsal column, the fourth segment S4 formed by the lumbar column, the fifth segment S5 formed by the pelvis, a sixth segment S6 formed by the femur, and the upper part of a seventh segment S7 formed by the tibia can be seen. The respective intermediate articulations A1, A2, A3, A4, A5 and A6 can be seen, as illustrated in the figure.

A segment of the body, comprising the skeleton and the other organs located in the same height region of the body, corresponds to each segment S1-S7. In general, the other organs are offset with respect to the skeleton.

The assumption is made that the center of gravity of each of the segments of the body is aligned with the vertical passing through the center of gravity G of the whole. This vertical is represented by the overall axis of gravity 5 as determined by the device of FIG. 7, as indicated above.

The head segment S1 is articulated on the articulation point A1. Together, the head segment S1 and the cervical segment S2 are articulated on the articulation point A2. Together, the head segment S1, the cervical segment S2 and the dorsal segment S3 are articulated on the articulation point A3. The unit formed by the head segment S1, the cervical segment S2, the dorsal segment S3 and the lumbar segment S4 is articulated on the articulation point A4, and so on.

Each body segment has its own weight. Previously published anatomical studies define each segment's weight as a proportion of the total weight of the body.

Figure 2:
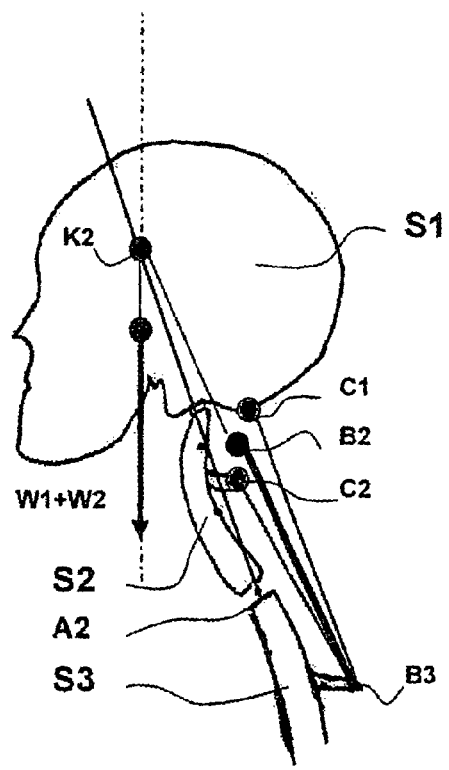
FIG. 2 is a side view illustrating the partial balancing by the forces of gravity, the muscular forces and the contact forces between an upper subunit, consisting of the head and the cervical segment, and the adjacent body segment below.

The model of balancing the upper two segments S1 and S2 on the third segment S3, as illustrated in FIG. 2, will now be considered as an example. The unit S1 and S2 can rotate about the articulation A2 of the dorsal segment S3, in the plane of the figure. The unit S1 and S2 is subject to a force of gravity W1+W2, the relative value of which with respect to the known total weight W is known from the previous works on anatomy. This force of gravity W1+W2 is applied at a local center of gravity carried by the known direction of the overall axis of gravity 5.

This force of gravity W1+W2 causes the unit S1 and S2 to rotate about the articulation point A2 identified on the radiographic exposure, and therefore identified on the digitized radiographic image. Its rotary action is compensated for with the force exerted by the muscles. Two muscular bundles are involved in the proposed example: one is inserted on the segment S3 level with the third dorsal vertebra, the insertion being designated by the reference B3 in FIG. 2, and is inserted on the head S1 at the point C1; another bundle extends from the same dorsal insertion B3 to the fourth cervical vertebra, on which it is inserted at the point C2. The resultant action of the muscles combines the action of the two bundles, and it is found that the resultant force of the muscles follows an average direction B3B2 thus determined from the radiographic exposure.

The task is therefore to solve a two-dimensional static mechanical problem involving three forces:

a force of gravity, of which the vertical direction is known, that is to say the direction of the overall axis of gravity, and the value of which is known and equal to W1+W2, obtained from tables of known values;

a muscular force, the direction B3B2 of which is defined from the radiographic exposure or from the digitized radiographic image, and the magnitude of which is unknown; and a contact force passing through the articulation A2, the magnitude and the direction of which are unknown.

This problem is solved graphically, either directly on the radiographic exposure or, preferably, by vector calculation using the data of the digitized radiographic image.

In order to find the value of the balance force exerted by the muscles, a simple calculation consists in assuming that the balance force compensates for the rotational moment of the force of gravity applied to the whole, about the lower articulation A2. Accordingly, the direction of the two forces as well as the intensity of the force of gravity are known, and the intensity of the muscular force is deduced therefrom.

Figure 3:
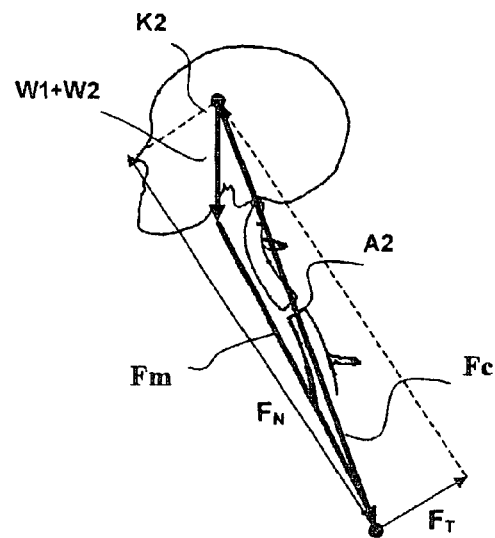
FIG. 3 illustrates the calculation of the forces in balancing the upper subunit consisting of the head and the cervical segment.

An overall solution method, as illustrated in FIG. 3, makes it possible to solve the problem and to simultaneously ascertain the muscular force and the contact force. To that end, it is assumed that the direction of the resultant muscular force B3B2 meets the overall axis of gravity 5 at the point K2. This point K2 also defines the direction of the contact force Fc, since the rotary moment of the three forces is thereby zero about the articulation A2.

The geometrical resultant of the force of gravity W1+W2 carried by the overall axis of gravity 5, of the muscular force Fm carried by the direction B3B2, and of the contact force Fc with a known direction A2K2, is then written as being zero. This calculation is displayed in FIG. 3, where Fc can be plotted in the direction A2K2, then W1+W2 in the vertical direction starting from K2, and Fm which joins the ends of the previous two vectors is deduced therefrom. The same determination of the force Fm may be carried out by calculation using the data of the digitized radiographic image. The magnitude of the muscular force Fm and the magnitude of the contact force Fc are obtained in this way. The latter may be resolved into a normal component FN perpendicular to the contact region in the articulation A2, and a tangential component FT parallel to the contact region A2. FN represents the pressure force due to the unit S1 and S2 on S3. FT represents the shear force in the contact region A2.

Figure 4:
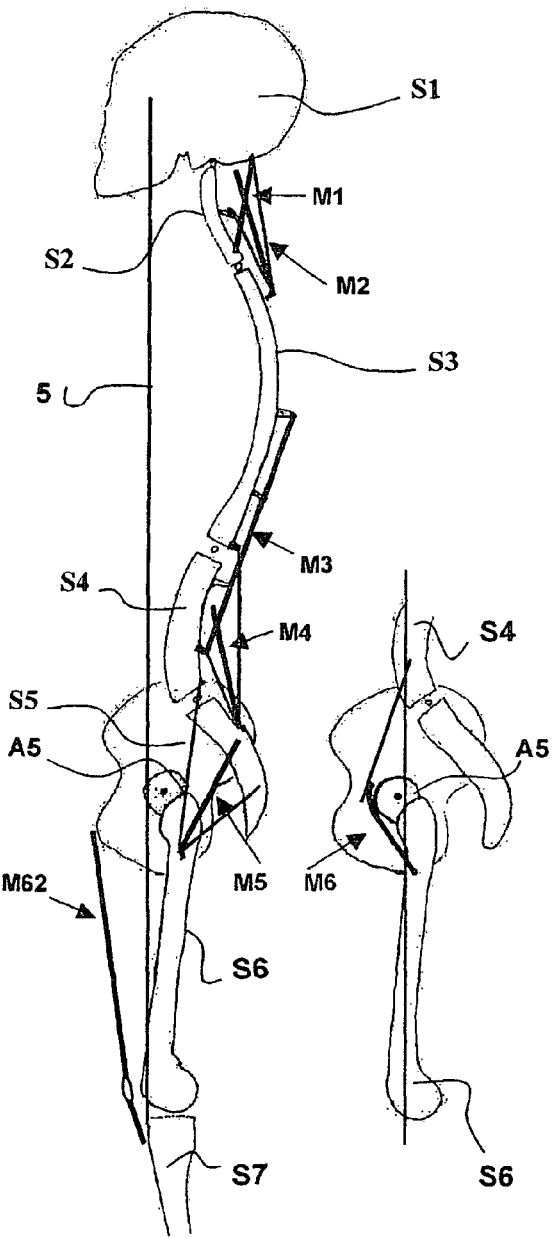
FIG. 4 is a side view illustrating the positions and directions of the main muscles providing the overall balance for the standing posture of the human body.

Among all the muscles that participate in balancing the posture, the invention chooses to consider the muscles which play an essential role. These muscles are illustrated in FIG. 4.

For instance, the muscle M1 consisting of the major complex is considered for the balancing of the head S1.

For the balancing of the cervical segment S2, the cervical part of the muscles of the nape of the neck is considered, such as the latissimus dorsi and the trapezius M2.

For the balancing of the dorsal segment S3, the muscle M3 consisting of the spinal erector is considered.

For the balancing of the lumbar segment S4, the lumbar lines M4 are considered, the bundles of which extend from the dorsal vertebra D12 to the lumbar vertebra L3.

For the balancing of the pelvis S5, the muscle M5 consisting of the gluteus maximus is considered, which is involved when the overall axis of gravity passes in front of the center of the femoral heads; this muscle is inserted in a fan shape along the sacral vertebra; when the overall axis of gravity passes behind the center of the femoral heads, the muscle M6 consisting of the psoas is considered, which extends around the femoral head.

For the balancing of the femurs, the rectus femoris M62 and the hamstring muscles M61 (see FIG. 6) are taken into account.

Figure 5:
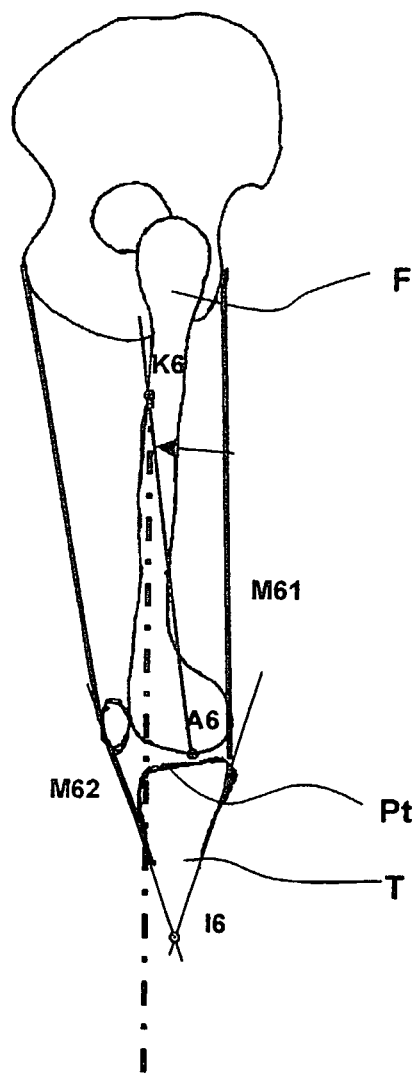
FIG. 5 is a side view illustrating determination of the resultant of the muscular forces in the region of the knee.
Figure 6:
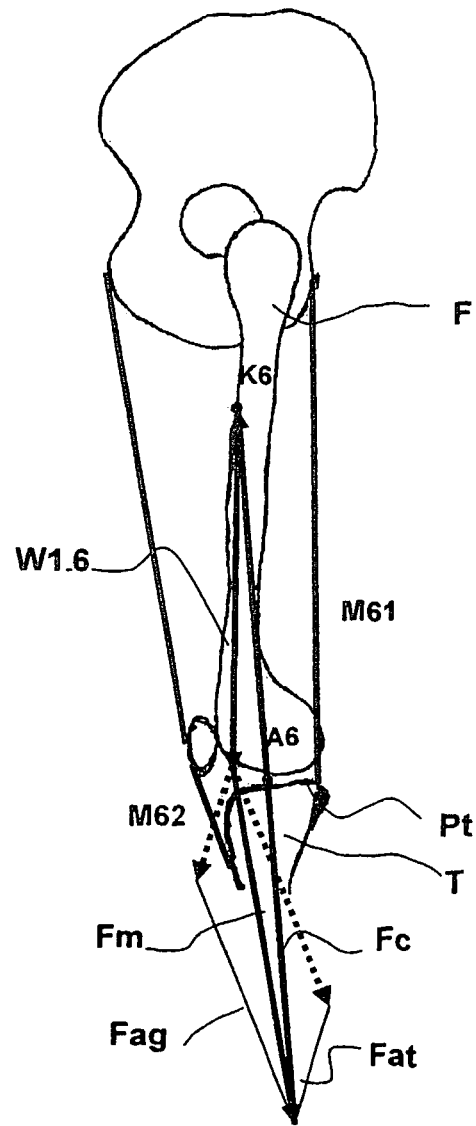
FIG. 6 is a side view illustrating the basic scheme for determining the balance forces in the region of the knee.

As a second example, FIGS. 5 and 6 illustrate evaluation of the balance forces of the knee articulation.

The knee is the articulation between the femur F and the tibia T. It has a special anatomical feature. The femur can rotate but also move along the tibial plateau Pt, so that it rotates and glides. This gliding is clinically demonstrated by the drawer test.

According to the invention, the contact between the femur F and the tibia T is assumed to take place without friction in order to comply with the condition of rolling and gliding. The agonist muscular forces (in the direction of the movement dictated by gravity) and antagonist muscular forces (in the opposite direction) are such that they are compatible with frictionless contact.

The magnitude and direction of the force of gravity W1-6 of the segments located above the knee are known. It is the sum of the forces of gravity W1, W2, W3, W4, W5 and W6. This force W1-6 is carried by the overall axis of gravity.

The direction of the contact force Fc is known: it extends through the point A6 of contact between the femur F and the tibia T, which can be identified on the radiograph. It is perpendicular to the tibial plateau Pt, which can also be seen on the radiograph. The rectus femoris M62 produces an agonist force Fag, while the hamstrings M61 produce an antagonist force Fat, of which the directions of action on the tibia T are illustrated in FIG. 5 and intersect at the point 16.

The procedure for determination of the forces is similar to that above, as will now be indicated with reference to FIGS. 5 and 6. The direction of the contact force Fc, which passes through the point of contact A6, intersects the overall axis of gravity 5 at the point K6. The resultant Fm of the agonist and antagonist muscular forces must pass through K6 in order to cancel the rotary effects of gravity. This resultant also passes through the point 16. The direction of the resultant of the muscular forces is therefore I6K6.

As illustrated in FIG. 6, the problem can be solved using a vector diagram, by applying the closure rule of the triangle of forces for a system in equilibrium. Knowing the force of gravity W1-6, and knowing the direction of the contact force Fc, the muscular force Fm is deduced therefrom and is then resolved in order to find the agonist force Fag and the antagonist force Fat. The same calculation may be carried out on the digitized radiographic image.

Reference will now be made to FIG. 7 once more, which illustrates the device according to an embodiment of the invention.

After having taken the radiographic image and identified the position of the overall axis of gravity 5, the operator proceeds to evaluate the muscular and pressure forces on the articulations.

According to a first option, he or she addresses the radiographic image as present on the sensitive plate 2 in the support means, and he or she picks the positions of the articulations, the segments and the anchoring points of the balancing tensor muscles on this radiographic image. The means 20 for digitizing the radiographic image of the subject simultaneously store the points designated by the operator, which are subsequently used for the force calculations.

According to another option, the operator views the digitized radiographic image as well as the position of the overall axis of gravity 5 on a screen 23, and he or she uses the keyboard 22 or a mouse to pick the positions of the articulations, the segments and the anchoring points of the balancing tensor muscles on this radiographic image. The computation means 21 and the associated program allow the points designated by the operator to be stored for subsequently performing the force calculations.

A specific acquisition program allows the user to acquire an anatomical point on the digitized image of the film by using the mouse. Techniques taken from image processing are incorporated in the program in order to facilitate the acquisition of a point or detail. These are: a magnification effect, an increase in contrast in order to make a blurred exposure usable, aids for acquiring tangents to the bone profiles, or for reproducibly identifying the center of quasi-circular contours.

A digital representation program allows the user to visualize the various approaches for calculating the muscular and contact forces, based on the shape of the posture.

The program contained in the computation means 21 then makes it possible to carry out the force calculations according to the principle indicated above, and the program displays the results on the screen 23 or on any other suitable medium.

The program preferably takes into account the dimension of the horizontal-position dispersion ellipse of the overall axis of gravity in order to calculate a margin of error of the calculation of the muscular and contact forces.

According to the invention, by using a small number of points identified on the radiographs, which correspond to the articulation regions and to the directions of the balancing muscular actions, and by using the position of the subject's overall axis of gravity, the invention thus makes it possible to calculate the value of the main muscular force that balances a segment, or a set of previously balanced segments, with respect to the following segments. The magnitudes and directions of the contact forces induced in the articulation are also determined.

These evaluations employ simple laws from statics, and knowledge about the articulations from physiology.

The invention thus makes it possible to evaluate the muscular forces and pressure forces on the articulations, without requiring the use of sensors or other measuring instruments inside the human body.

The invention may be employed in the a priori evaluation of forces, in order to study a given posture.

The invention may also be employed for comparing a plurality of successive force evaluations of the same subject, for example before and after an operation, or before and after orthopedic treatment. It is thus possible to highlight variations which are much more significant than those which manifest the changes in morphology.

The present invention is not limited to the embodiments which have been explicitly described, but includes the different variants and generalizations thereof which are contained in the scope of the claims which follow.

The invention claimed is:

1. A method for evaluating the balance forces of a skeleton within a subject's body, comprising:
   a) arranging the subject between an X-ray source and a target plate in a reproducible position using a stabilizing support for stabilizing the subject;
   b) producing a radiographic image of the skeleton, the skeleton having segments articulated to one another, taken in a plane generally perpendicular to rotation axes of the articulations of the skeleton, c) simultaneously determining a position of an overall axis of gravity of the subject's body on the radiographic image, d) selecting the skeleton segments articulated to one another on the radiographic image, identifying positions of the segments and those of the articulations, and assigning a weight of the subject's body segment corresponding to each skeleton segment, e) identifying directions and selecting anchoring points on the radiographic image of main tensor muscles balancing the subject's skeleton including a spinal erector muscle and a muscle extending from a dorsal vertebra D12 to the lumber vertebra L3, and f) determining an intensity of a restoring force exerted by the main tensor muscles by calculation based upon the identified directions and anchoring points of the main tensor muscles, wherein the restoring force compensates for a rotational moment of the force of gravity applied to each skeleton segment about a lower articulation of said skeleton segment, wherein the subject is placed in a stable balance position, successive positions of the overall axis of gravity for a few seconds are stored with a frequency of several acquisitions per second, wherein the stored positions comprise an elliptical cloud of positions, and wherein a dispersion ellipse which envelopes said cloud of positions is determined, and wherein radiographic images corresponding to an overall axis of gravity whose position lies in the dispersion ellipse are selected.

2. The method as claimed in claim 1, wherein a margin of error in an evaluation of the restoring or bearing forces is determined by calculation as a function of the dispersion ellipse.

3. A method for evaluating the balance forces of a skeleton within a subject's body, comprising:

a) producing a radiographic image of the skeleton, the skeleton having segments articulated to one another, taken in a plane generally perpendicular to rotation axes of the articulations of the skeleton, b) simultaneously determining a position of an overall axis of gravity of the subject's body on the radiographic image, c) selecting at least three skeleton segments articulated to one another by at least two joints on the radiographic image, identifying positions of the segments and those of the articulations, and assigning a weight of the subject's body segment corresponding to each skeleton segment, wherein the at least three skeleton segments are selected from the group consisting of the head, the cervical segment, the dorsal segment, and the lumbar segment, d) identifying directions and selecting anchoring points on the radiographic image of the main tensor muscles balancing the subject's skeleton including a spinal erector muscle and a muscle extending from a dorsal vertebra Dl2 to the lumber vertebra L3, and e) determining an intensity of a restoring force exerted by the main tensor muscles by calculation based upon the identified directions and anchoring points of the main tensor muscles, wherein the restoring force compensates for a rotational moment of the force of gravity applied to each skeleton segment about a lower articulation of said skeleton segment, wherein a bearing force of each skeleton segment on its lower articulation is determined by calculation, wherein the bearing force is equal to a resultant of the force of gravity and of the restoring force applied to the skeleton segment, wherein the subject is placed in a stable balance position, successive positions of the overall axis of gravity for a few seconds are stored with a frequency of several acquisitions per second, wherein the stored positions comprise an elliptical cloud of positions, and wherein a dispersion ellipse which envelopes said cloud of positions is determined, and wherein radiographic images corresponding to an overall axis of gravity whose position lies in the dispersion ellipse are selected.

4. A device for evaluating the balance forces of the skeleton of a subject, the skeleton having segments articulated to one another and the subject having balancing tensor muscles attached to the skeleton at anchoring points, comprising:

an X-ray source and support means for a target plate sensitive to X-rays, a subject support plate for supporting the subject in a fixed position between the X-ray source and the support meanns for the target plate and to generate image position signals of a horizonal position of an overall axis of the subject, a stabilizing support adjacent the support plate configured for use by the subject to stabilize himself or herself on the subject support plate, means for digitizing a radiographic image of the subject on the target plate, so as to generate a digitized radiographic image which is stored in a suitable memory, means for superimposing the digitizing image of a shadow, cast by the overall axis of gravity on the target plate, onto the digitized radiographic image of the subject, means for selecting, on the digitized radiographic image, the articulated skeleton segments and their articulations, and the anchoring points of the balancing tensor muscles, and computation means for calculating the intensity of a restoring force exerted by the balancing tensor muscles including a spinal erector muscle and a muscle extending from a dorsal vertebra D12 to the lumber vertebra L3, wherein the restoring force compensates for a rotational moment of a force of gravity applied to each skeleton segment about the lower articulation of said skeleton segment;

means for evaluating variations in a subject's vertical posture by dimensions of a horizonal-position dispersion ellipse of the subjects's overall axis of gravity, when the subject occupies a stable position.

5. The device as claimed in claim 4, wherein the computation means further includes:

means for selecting the positions on the radiographic image of the articulations, the segments and the anchoring points of the balancing tensor muscles; and means for causing the means for digitizing the radiographic image of the subject to store the selected positions in the memory.

6. The device as claimed in claim 4, wherein the computation means further includes:

means for causing the digitized radiographic image to display on a screen, means for selecting by an input/output device the positions of the articulations, the segments and the anchoring points of the balancing tensor muscles on said digitized radiographic image; and means for storing the coordinates of the selected points.

7. A device for evaluating the balance forces of the skeleton of a subject, the skeleton having segments articulated to one another and the subject having balancing tensor muscles attached to the skeleton at anchoring points, comprising:

an X-ray source and support means for a target plate sensitive to X-rays, a subject support plate for supporting the subject in a fixed position between the X-ray source and the support means for the target plate and to generate image position signals of a horizontal position of an overall axis of gravity of the subject, a stabilizing support adjacent the support plate configured for use by the subject to stabilize himself or herself on the subject support plate, means for digitizing a radiographic image of the subject on the target plate, so as to generate a digitized radiographic image which is stored in a suitable memory, means for superimposing the digitized image of a shadow, cast by the overall axis of gravity on the target plate, onto the digitized radiographic image of the subject, means for selecting, on the digitized radiographic image, the articulated skeleton segments and their articulations, and the anchoring points of the balancing tensor muscles, and computation means for calculating the intensity of a restoring force exerted by the balancing tensor muscles including a spinal erector muscle extending from a dorsal vertebra D12 to lumber vertebra L3, wherein the restoring force compensates for a rotational moment of a force of gravity applied to each skeleton segment about the lower articulation of said skeleton segment, wherein the computation means further includes:

means for selecting the positions on the radiographic image of the articulations, the segments and the anchoring points of the balancing tensor muscles;

means for causing the means for digitizing the radiographic image of the subject to store the selected positions in the memory; and means for calculating a margin of error of a calculation of muscular and contact forces taking into account a dimension of a horizontal-position dispersion ellipse of the overall axis of gravity.

8. The device as claimed in claim 5, wherein the computation means further includes means for calculating a margin of error of a calculation of muscular and contact forces taking into account a dimension of a horizontal-position dispersion ellipse of the overall axis of gravity.

9. The device as claimed in claim 5, wherein the computation means further includes means for calculating a margin of error of a calculation of muscular and contact forces taking into account a dimension of a horizontal-position dispersion ellipse of the overall axis of gravity.

10. A device for evaluating the balance forces of the skeleton of a subject, the skeleton having segments articulated to one another and the subject having balancing tensor muscles attached to the skeleton at anchoring points, comprising:

an X-ray source;

a target plate sensitive to X-rays from the X-ray source;

a subject support plate configured to support the subject in a stable position between the X-ray source and the target plate, wherein the subject support plate includes a plurality of force sensors configured to provide data for the calculation of a horizontal position of an overall center of gravity of the subject;

a computer configured to process data obtained by the force sensors and being configured to calculate the overall center of gravity of the subject, the computer being configured to generate image position signals of the horizontal position of the overall center of gravity of the subject;

a stabilizing support adjacent the support plate configured for use by the subject to stabilize himself or herself on the subject support plate;

a digitizer configured to digitize a radiographic image of the subject on the target plate, so as to generate a digitized radiographic image which is stored in a suitable memory of the computer;

wherein the computer is configured to superimpose the digitized image of a shadow, cast by the overall axis of gravity on the target plate, onto the digitized radiographic image of the subject, the computer also being configured in a manner that permits manipulation of the digitized image by a magnification effect;

an input device associated with the computer and configured in a manner that permits selecting, on the digitized radiographic image, the articulated skeleton segments and their articulations, and the anchoring points of the balancing tensor muscles;

the computer being configured to calculate the intensity of a restoring force exerted by the balancing tensor muscles including a spinal erector muscle and a muscle extending from a dorsal vertebra D12 to the lumber vertebra L3, wherein the restoring force compensates for a rotational moment of a force of gravity applied to each skeleton segment about the lower articulation of said skeleton segment.

11. The device of claim 10, wherein the digitizer comprises a scanner.

12. The device of claim 10, wherein the computer is configured in a manner that permits manipulation of the digitized image by at least one of: an increase in contrast in order to make a blurred exposure usable; an aid for acquiring tangents to the bone profiles; and an aid for reproducibly identifying the center of quasi-circular contours.

* * * * *